United States Patent [19]

Cosgrove

[11] Patent Number: 5,752,526
[45] Date of Patent: May 19, 1998

[54] MINIMALLY INVASIVE CARDIAC SURGERY PROCEDURE

[75] Inventor: Delos M. Cosgrove, Hunting Valley, Ohio

[73] Assignee: The Cleveland Clinic Foundation, Cleveland, Ohio

[21] Appl. No.: 603,313

[22] Filed: Feb. 19, 1996

[51] Int. Cl.$^6$ ..................................................... A61F 2/24
[52] U.S. Cl. ................................ 128/898; 623/2; 623/66
[58] Field of Search ...................... 128/897–98; 623/1–3, 623/66

[56] References Cited

U.S. PATENT DOCUMENTS 5,041,130   8/1991   Cosgrove et al. .
5,571,215   11/1996   Sterman et al. ............................ 623/2

FOREIGN PATENT DOCUMENTS

WO 95/15715   6/1995   WIPO .

*Primary Examiner*—John P. Lacyk
*Attorney, Agent, or Firm*—Michael A. Lechter; David E. Rogers

[57] ABSTRACT

A minimally invasive approach for surgery on portions of the heart and great vessels located between a point approximately three centimeters above supra annular ridge and the mid ventricular cavity. A parasternal incision is made extending across a predetermined number of costal cartilage, e.g., a right parasternal incision extending from the lower edge of the second costal cartilage to the superior edge of the fifth costal cartilage. One or more costal cartilages, e.g., the third and fourth, are then excised to provide access to the portion of the heart or great vessels of interest, and a desired procedure completed. A minimally invasive procedure for repair or replacement of the aortic valve is disclosed.

12 Claims, 6 Drawing Sheets

MINIMALLY INVASIVE CARDIAC SURGERY PROCEDURE

BACKGROUND OF THE INVENTION

1. Field of the Invention

The present invention relates to surgical procedures and, more specifically, to minimumly invasive procedures for surgery involving portions of the heart and great vessels located between a point approximately 3 centimeters above supra annular ridge and the mid ventricular cavity, such as, for example, procedures for repair and replacement of the aortic valve.

2. Description of the Related Art

Various types of surgical procedures are performed on the heart and the great vessels. Many of such procedures, particularly those involving the aorta, and aortic valve employ a gross thoracotomy, e.g., a median sternotomy, in order to gain access to the involved portion of the heart or vessel. In other words, the procedures entail splitting open the patient's chest. Such procedures cause significant trauma to the patient, and recovery time.

An example is the conventional procedure for aortic valve surgery. The patient is anesthetized, and the skin is incised from the top of the sternum to a point located a predetermined distance, e.g., approximately two inches, below the bottom of the sternum. The sternum is then split longitudinally, using a saw or other cutting implement. A spreader is placed within the chest cavity and the opposing halves of the rib cage spread apart to expose the thoracic cavity. The tissues around the heart are divided, opening the pericardial sack. A cardiopulmonary bypass is initiated through direct aortic and right atrial cannulation (that is, circulation to a heart-lung machine is established through an arterial-returning catheter disposed in the aorta and a venous drainage catheter in the right atrium), the aorta is clamped (typically between the brachycephalic artery and the coronary ostia) to exclude the heart from the circulation, and. The cardiac function is then arrested, i.e., the heart is stopped, by infusion of a cardioplegia fluid, such as a cold potassium solution. The aorta is then opened. The valve is then repaired, or if to be replaced, excised and a replacement valve sewn in. Any air that may have accumulated in the heart during the procedure is then removed from the heart and the aorta closed with sutures. The clamp is then removed, patient weaned from the heart-lung machine, tubes removed from the aorta, the sternum wired back together and the skin closed with sutures.

Such procedures are particularly traumatic. Incisional pain tends to require significant postoperative analesia and postoperative discomfort tends to result in significant patient morbidity and lengthy hospital stays. In addition, because the pericardial sack is opened underlying the sternum, after the procedure the heart has a tendency to become adherent to the sternum. This can be problematical in the event of subsequent procedures.

The desirability of avoiding the use of median sternotomy, and other gross thoracotomy procedures, in connection with surgery on the heart and great vessels has been recognized. For, example, techniques have been proposed in which a scope is inserted through a percutaneous intercostal penetration in the patient's chest (an incision between the ribs) to observe internal procedures performed by instruments introduced into the chest with the scope, or through cannula disposed in other intercostal spaces, i.e., between two adjacent ribs. Such techniques and instruments for performing such techniques within the heart and great vessels is described in International Publication WO 95/15715 by Sterman et al., published Jun. 15 1995. However, such techniques require special instrumentation and special skills to perform, and may extend the time the heart is arrested and the duration of the procedure.

SUMMARY OF THE INVENTION

The present invention provides a minimally invasive approach for surgery on portions of the heart and great vessels located between a point approximately three centimeters above supra annular ridge and the mid ventricular cavity. In accordance with one aspect of the present invention, a parasternal incision is made extending across a predetermined number of costal cartilage, e.g., a right parasternal incision extending from the lower edge of the second costal cartilage to the superior edge of the fifth costal cartilage. One or more costal cartilages, e.g., the third and fourth, are then excised to provide access to the portion of the heart or great vessels of interest, and a desired procedure completed.

BRIEF DESCRIPTION OF THE DRAWING

A preferred exemplary embodiment of the present invention will hereinafter be described with reference to the appended drawing, wherein like denominations indicate like elements, and.

DETAILED DESCRIPTION OF A PREFERRED EXEMPLARY EMBODIMENT

Figure 1:
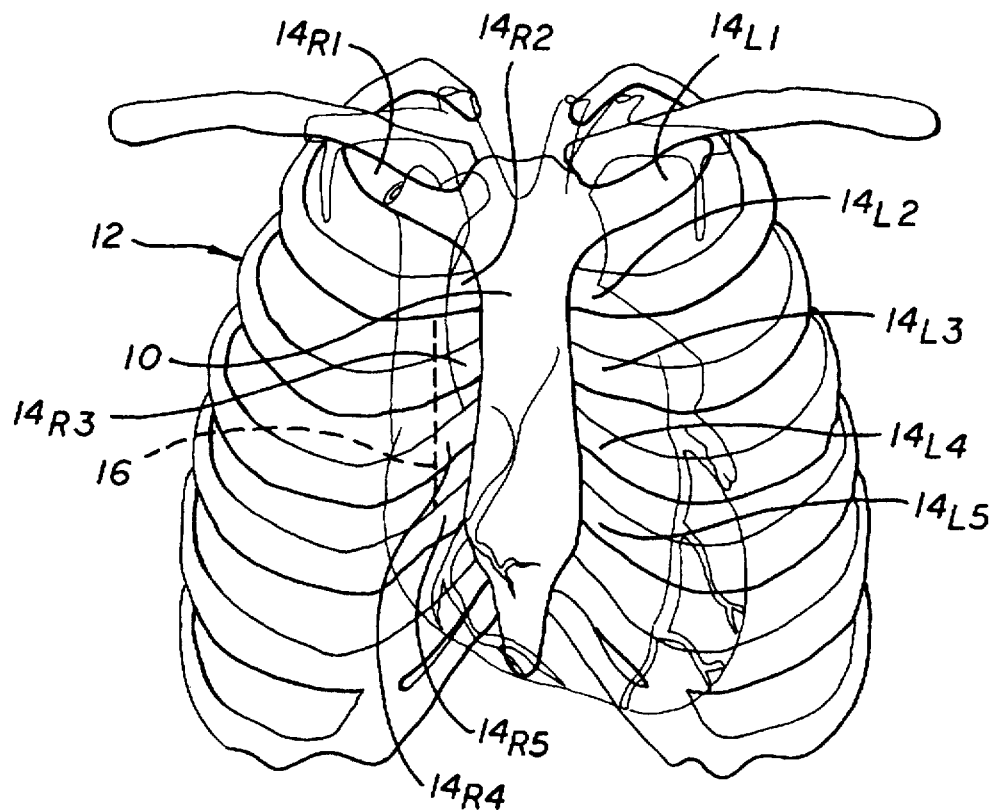
FIGS. 1 and 1A are schematic illustrations depicting a human chest and the disposition of a right parasternal incision in connection with an aortic surgery procedure in accordance with the present invention.

Referring now to FIG. 1, in a typical human, a sternum 10, a planary bone structure centrally disposed in chest, is connected to a plurality of ribs 12 by respective costal cartilages $14_{R1}$, $14_{R2}$, $14_{R3}$, $14_{R4}$, $14_{R5}$ and $14_{L1}$, $14_{L2}$, $14_{L3}$, $14_{L4}$, $14_{L5}$. The heart and great vessels are located within a tissue sack (pericardium), located beneath the sternum, extending laterally under the costal cartilages and ribs, with the aorta disposed in part underlying the second and third right costal cartilages $14_{R2}$ and $14_{R3}$, and a portion of the right coronary artery located generally underlying the vicinity of the fourth and fifth right costal cartilages $14_{R4}$ and $14_{R5}$.

Figure 1A:
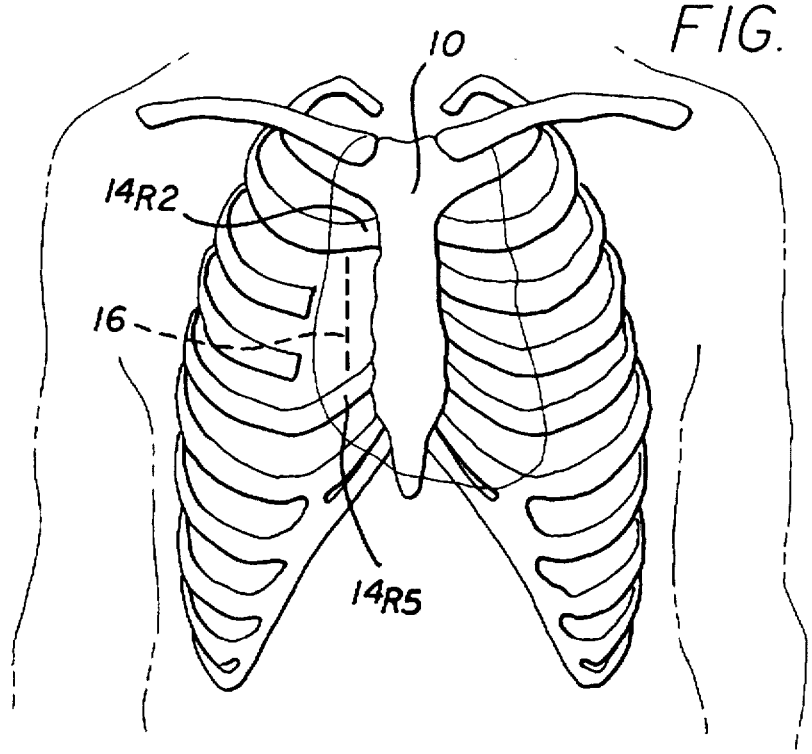

In accordance with one aspect of the present invention, it has been determined that a surgery on portions of the heart and great vessels located between a point approximately three centimeters above supra annular ridge and the mid ventricular cavity, can be effected with minimal invasion, without a median sternotomy, or other gross thoracotomy, by, as illustrated in FIG. 1A, making a relatively short parasternal incision 16 extending across a predetermined number of costal cartilage, e.g., a right parasternal incision extending from the lower edge of the second costal cartilage $14_{R2}$ to the superior edge of the fifth costal cartilage $14_{R5}$, and removing one or more costal cartilages, e.g., the third and fourth costal cartilages, $14_{R3}$ and $14_{R4}$. It has been determined that over a period of time the chest wall in the area of the resected cartilages becomes stable secondary to scarring of the remaining tissue. In effect, scar tissue resulting from the procedure functionally replaces the excised cartilage, providing a relatively rigid chest wall.

This procedure can be readily employed to perform operations on structures located on portions of the heart and great vessels located between a point approximately three centimeters above supra annular ridge and the mid ventricular cavity. As will be more fully described, the procedure is of particular utility with respect to surgery to repair or replace the aortic valve. Further, in some instances, the minimumally invasive approach of the present invention can be employed to effect a variety of other operations, such as, for example: septal myectomy (excision of a portion of the muscle just below the aortic valve to correct an obstruction to the outflow of the heart); closure of a ventricular septal defect (e.g., a congenital hole in the heart); and correction of aneurysms.

The minimumally invasive approach of the present invention is particularly advantageous as compared to a median sternotomy. In addition to decreased trauma to the patient, and the attendant benefits, the minimumally invasive technique provides additional advantages in the event of repeat surgery. Since, pericardial sack underlying the sternum opened under the sternum in a median sternotomy, after the procedure the heart has a tendency to adhere to the sternum. This can be problematical in the event of subsequent procedure; there is a risk of cutting into the heart when sawing through the sternum during the subsequent operation. In contradistinction, in the procedure according to the present invention, the pericardium underlying the sternum remains intact; normal tissue is retained between the sternum and the heart and there is no risk of the heart adhering to the sternum. A series of operations are relatively common in connection correction of congenital heart disease.

As noted above, the minimumally invasive approach of the present invention is of particular utility with respect to surgery to repair or replace the aortic valve. Specifically, in the context of exemplary surgery to replace an aortic valve, the patient is anesthetized and intubated, and placed supine on the operating room table. Preferably, defibrillator pads are placed on the patient's back and anterior left chest, and a transesophageal echocardiography probe is placed to access the etiology of the aortic valve disease and to assist in removing air from the heart after completion of the operation.

Figure 2:
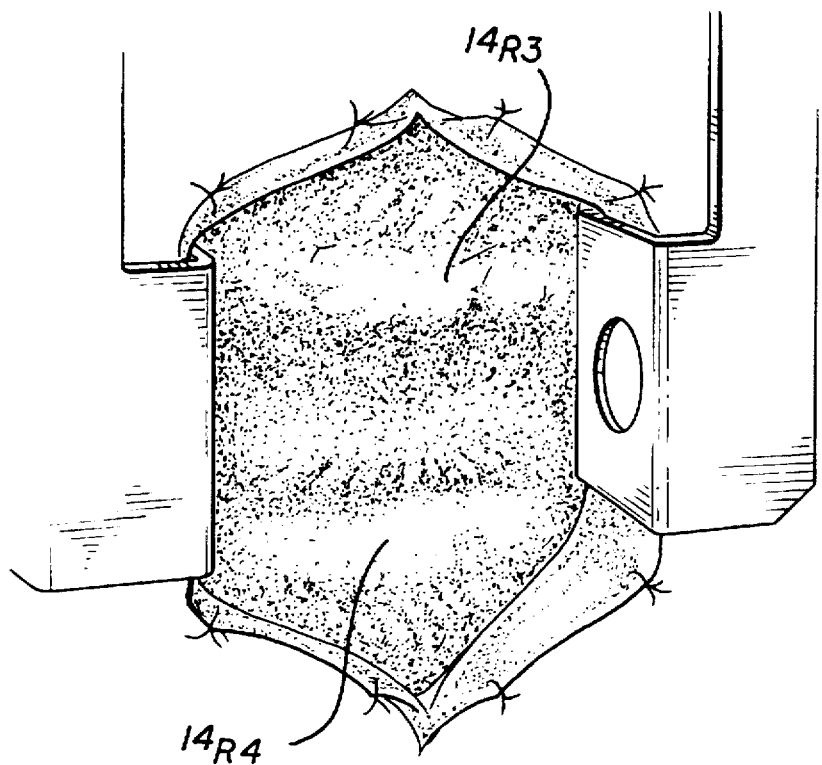
FIG. 2 is an pictorial illustration depicting the right parasternal incision of FIG. 1 showing respective costal cartilages.
Figure 3:
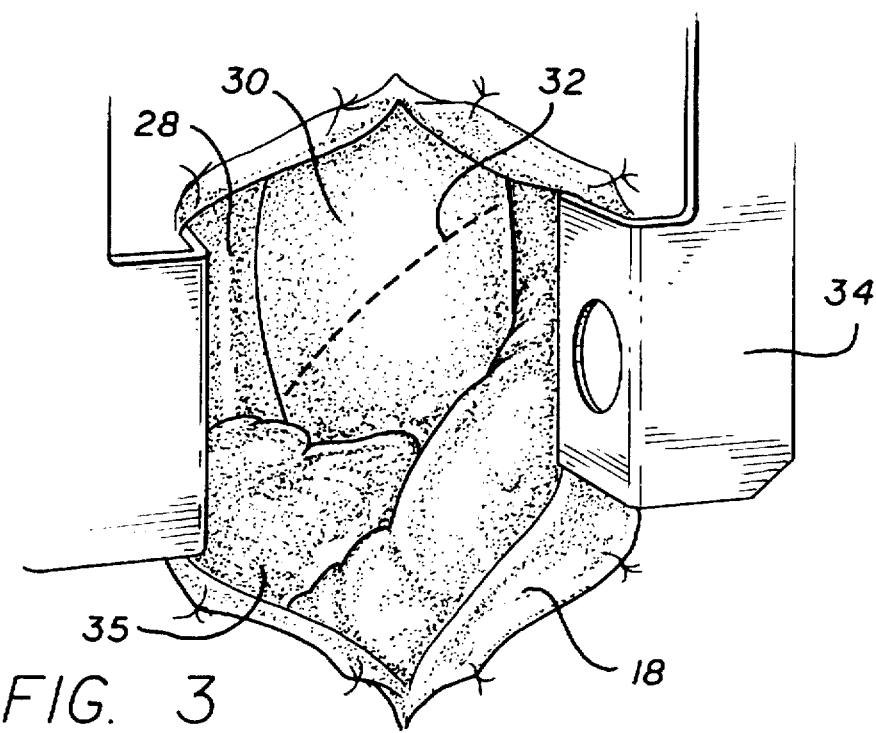
FIG. 3 is an pictorial illustration depicting the right parasternal incision of FIG. 1 after respective costal cartilage units are excised and incision retracted.

Referring to FIGS. 1 and 1A, a right parasternal incision is made extending from the lower edge of the second costal cartilage $14_{R2}$ to the superior edge of the fifth costal cartilage. The pectoralis major muscle is divided, exposing the second, third, and fourth intercostal spaces, and the third and fourth costal cartilages $14_{R3}$ and $14_{R4}$, as shown in FIG. 2. The third and fourth costal cartilages $14_{R3}$ and $14_{R4}$ are totally excised (FIG. 1A). The right internal thoracic artery is ligated just below the second costal cartilage $14_{R2}$ and just above the fifth costal cartilage $14_{R5}$. Intercostal muscles and pleura are incised lateral to the edge of the sternum, entering the right pleural cavity. As shown in FIG. 3, the pericardium 18 is then incised, exposing the ascending aorta 30, and is stitched back. The incision is held open using a conventional chest retractor 34.

Figure 4:
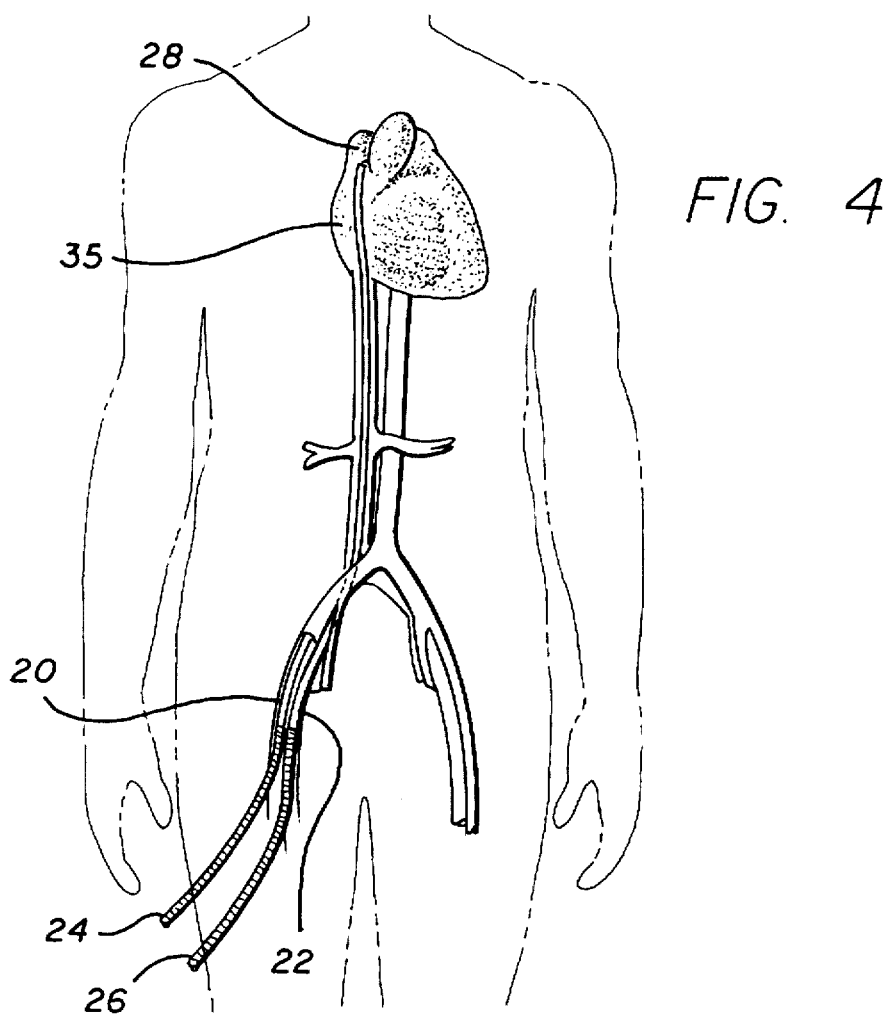
FIG. 4 is an schematic illustration depicting the disposition of respective by-pass cannula employed in connection with an aortic surgery procedure in accordance with the present invention.
Figure 5:
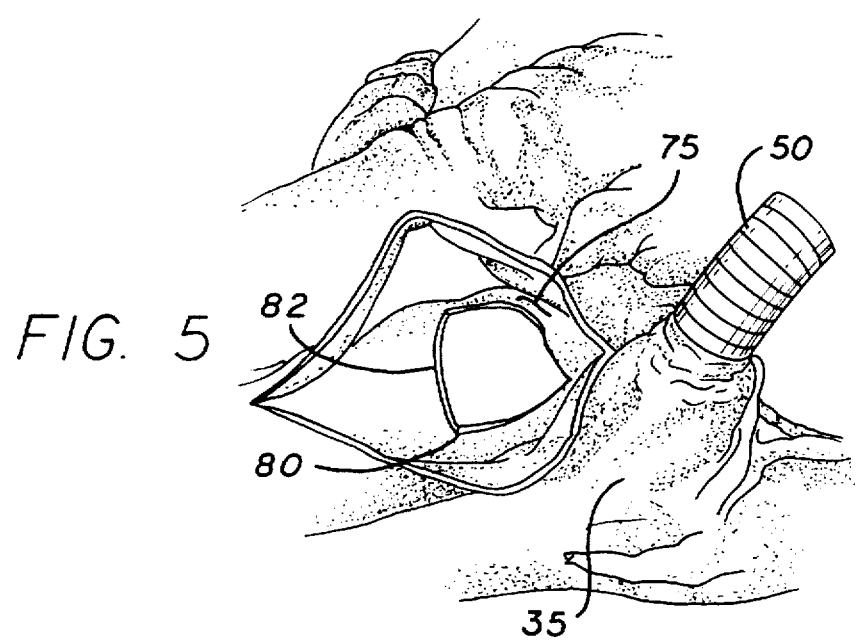
FIG. 5 is an schematic illustration depicting an alternative disposition of respective by-pass cannula employed in connection with an aortic surgery procedure in accordance with the present invention.
Figure 6:
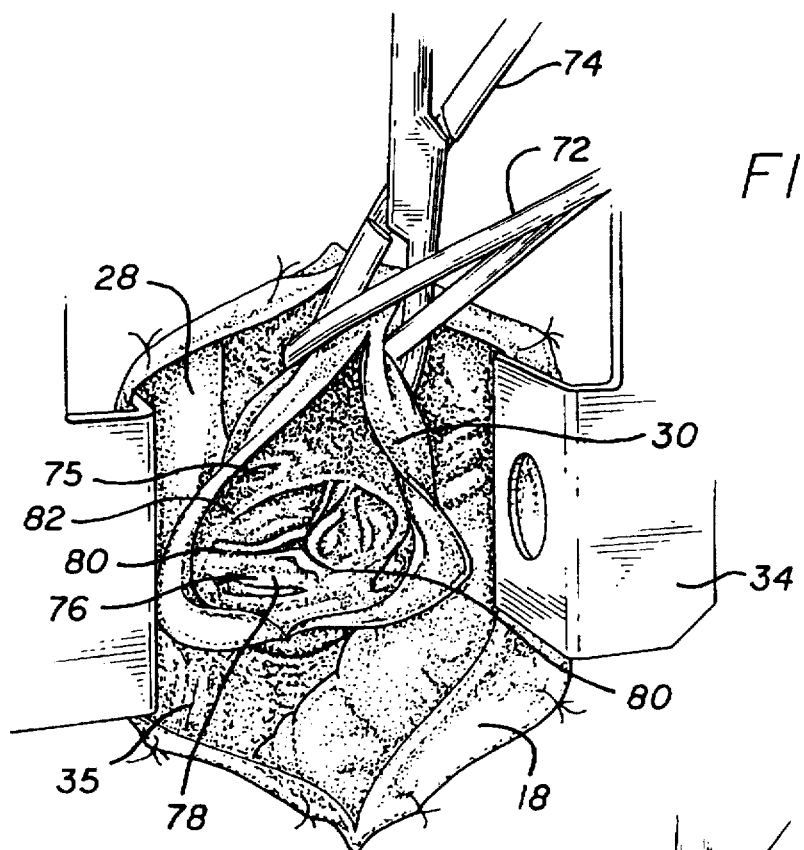
FIG. 6 is an pictorial illustration depicting the right parasternal incision of FIG. 1 after the aorta is opened to expose the aortic valve.

A cardiopulmonary by-pass is then established. Referring now to FIG. 4, a common femoral artery 20 and vein 22 are exposed and, after infusion of an anti-coagulant, e.g., heparinization, are cannulated; Catheters 24 and 26 are placed in femoral artery 20 and in femoral vein 22, respectively. Adequate venous drainage may be obtained by utilizing a long venous cannula 26 disposed so that the tip of the cannula passes through the right atrium 35 and preferably into the superior vena cava 28 (FIG. 3). Alternatively, as illustrated in FIG. 5, venous return can be effected by introducing an appropriate catheter 50 into the right atrial appendage 35. (The anatomy depicted in FIG. 5 illustrates the results of additional steps in the procedure, as will be explained). Catheters 24 and 26 direct the blood to a conventional heart-lung machine (not shown) which oxygenates the blood and pumps it back under pressure to the patient. Referring to FIG. 6, after catheters 24 and 26 are placed, the heart is excluded from circulation; aorta 30 is suitably encircled with umbilical tape 72 and the ascending aorta 30 cross clamped with a right angle clamp 74.

With continued reference to FIG. 6, the aorta is then incised (along line 32; FIG. 3) to expose the coronary ostia 75 and the aortic valve 76. Aortic valve 76 includes a plurality, typically three, of leaflets (valve cusps) 78, joined at respective commissures 80, and surrounded by a relatively fibrous aortic annulus 82.

Figure 7:
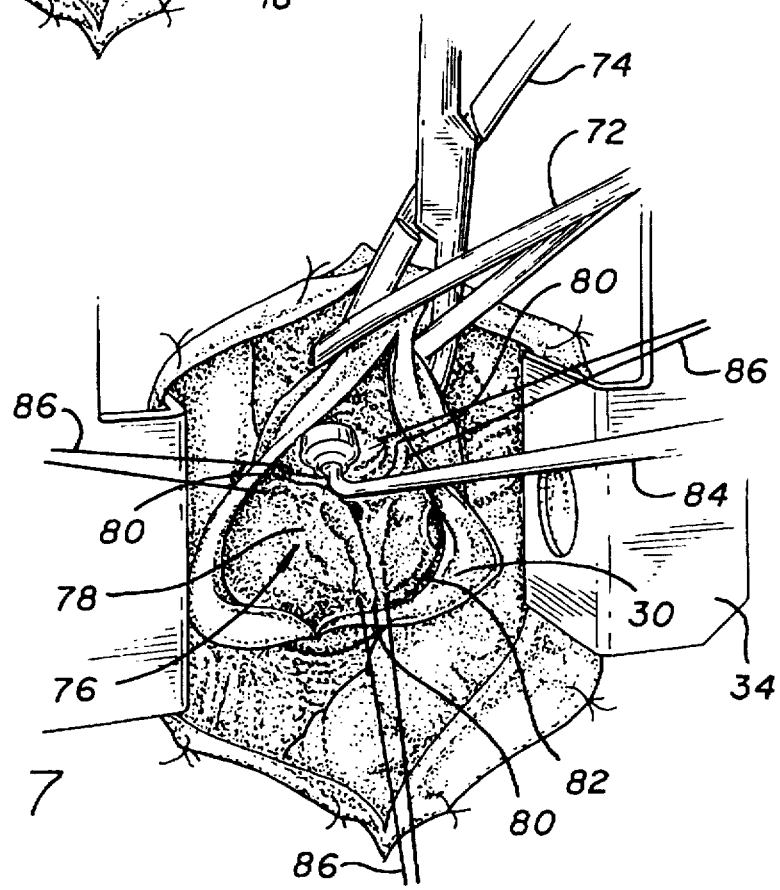
FIG. 7 is an pictorial illustration of injection of cardioplegia into the coronary ostia.

Cardiac function is arrested, by e.g., by administering cardioplegia into the ascending aorta. Referring now to FIG. 7, after performing the aortotomy, a suitable cardioplegia is introduced into the left coronary artery. Preferably, a suitable cardioplegia fluid, such as a cold potassium solution is infused through a catheter 84 inserted in coronary ostia 75. Sutures 86 are the suitably placed just above each commissure 80, and clamped under tension to a drape (not shown) surrounding the operating site. This elevates the aortic root (e.g., aortic annulus 82) into the operative field.

Figure 8:
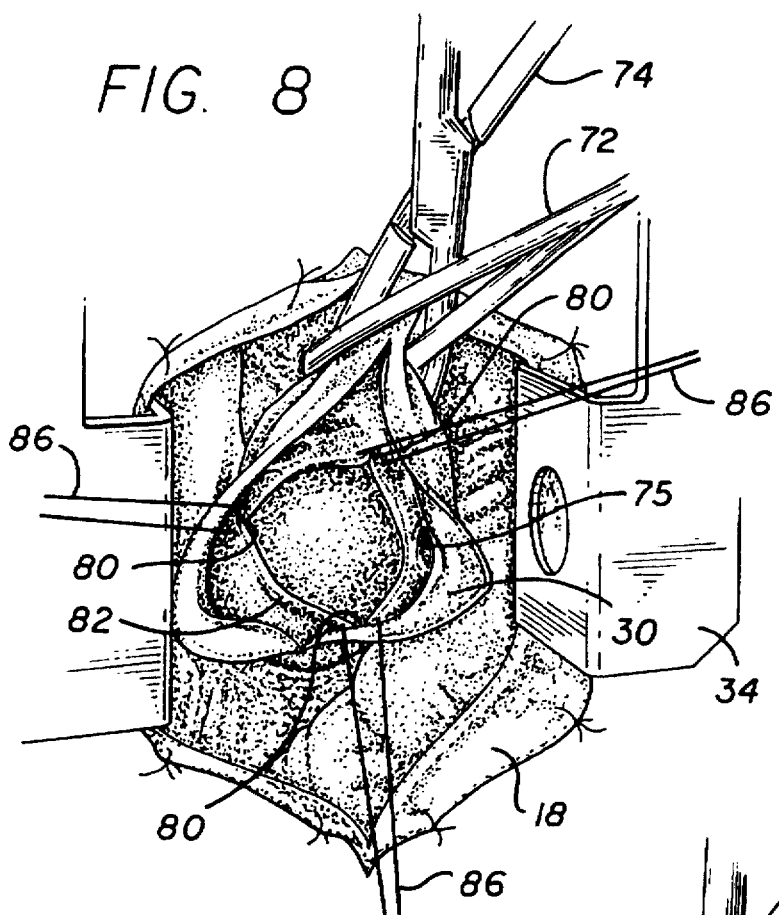
FIG. 8 is an pictorial illustration depicting the right parasternal incision of FIG. 1 after the aortic valve is removed, with traction sutures placed at the commissures.
Figure 9:
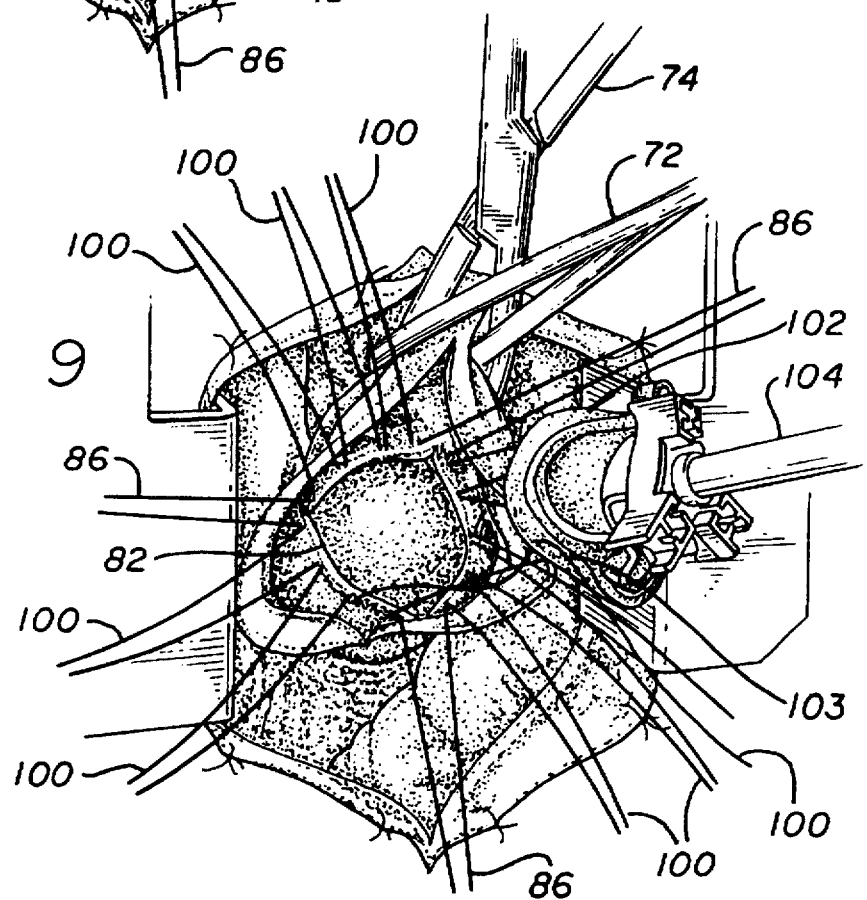
FIG. 9 is an pictorial illustration depicting insertion of an aortic valve prosthesis.

Aortic valve 76 is then either repaired or replaced. For example, referring to FIGS. 8 and 9, where a valve replacement is effected, valve cusps 78 are excised, leaving aortic annulus 82 (FIG. 8; see also FIG. 5). A multiplicity of sutures 100 are then placed though aortic annulus 82 about the periphery of the void left by excision of the valve cusps 78 (FIG. 9). Sutures 100 are then employed to secure a suitable replacement valve 102. Replacement valve 102 may be, e.g., a bioprosthesis (cusps formed from animal tissue coupled to a suitable peripheral sewing ring, formed of e.g., polyester velour), a mechanical prosthesis (cusps formed from e.g., pyrolytic carbon with a suitable peripheral sewing ring 103, formed of e.g., polyester velour), or a homograft (e.g., formed from human tissue which was frozen in liquid nitrogen, then thawed). Attachment of the bioprosthesis and mechanical prosthesis replacement valves are suitably facilitated using a conventional insertion tool 104. Replacement valve 102 is typically attached to aortic annulus 82 by passing sutures 100 through sewing ring 103 of the replacement. A vent is intermittently placed into the left ventricle through the aortic annulus as needed.

Figure 10:
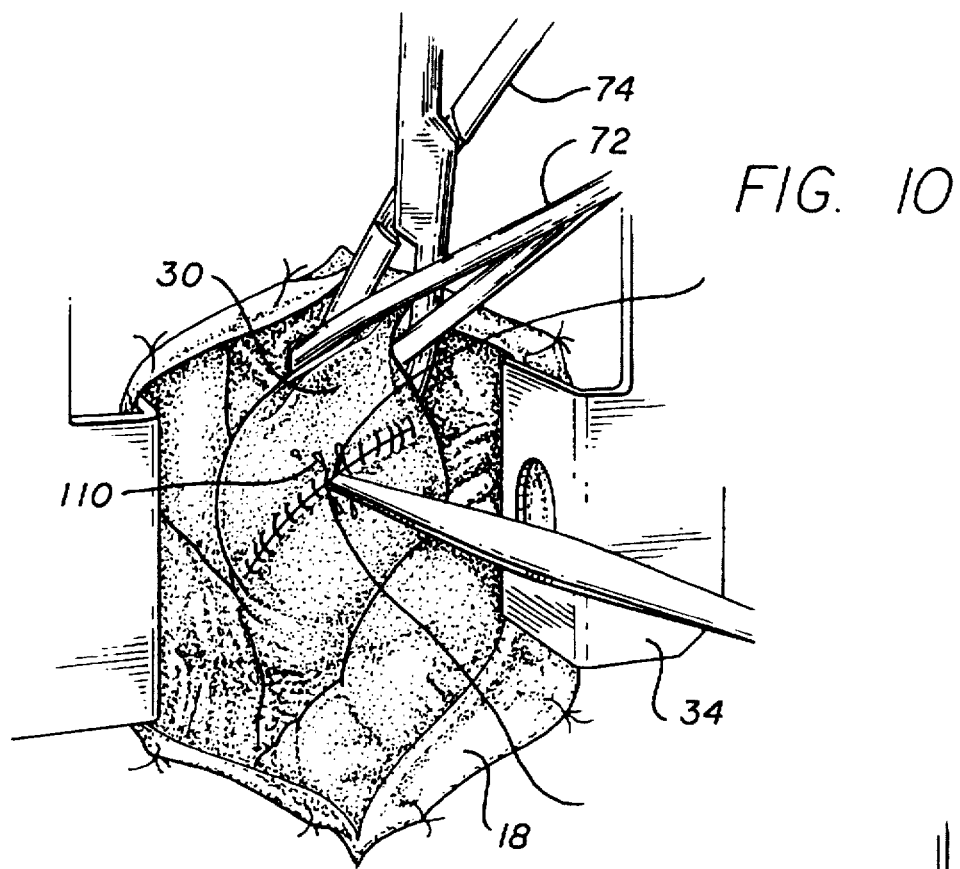
FIG. 10 is an pictorial illustration depicting closure of the aorta.

At the completion of the repair or replacement, the aortotomy is closed with sutures 110, as shown in FIG. 10. Air is then removed from the heart through the aorta with the assistance of the transesophageal echocardiography probe; all air bubbles are preferably removed from the heart by removing clamp 74 to restore blood flow, and inflating the lungs, until blood flows through sutures 110, then tightening the sutures.

Figure 11:
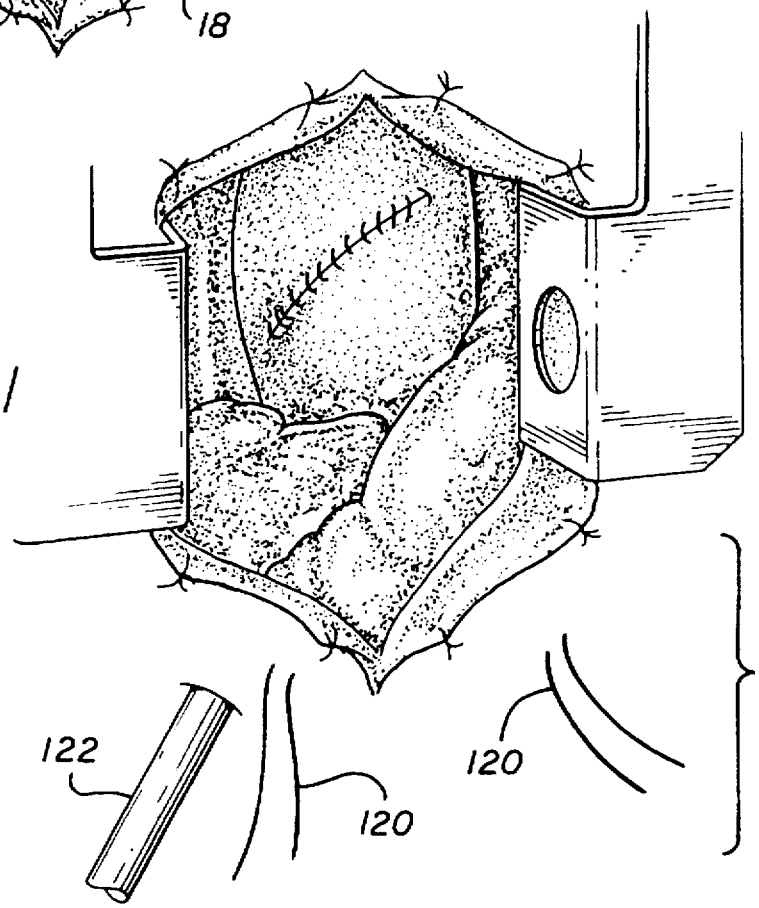
FIG. 11 is an pictorial illustration depicting disposition of temporary pacer leads and drainage tube.

Referring to FIG. 11, temporary pacemaker leads 120, 122 are placed on the on the atrium and on the ventricle to facilitate temporary pacing should it be necessary. The patient is weaned from cardiopulmonary bypass, the femoral vessels are decannulated and repaired; conventional right-sided pleural chest tubes 122 are placed, and the femoral and right parasternal incisions are closed, suitably by reapproximating the muscle, subcutaneous tissue and skin, in layers.

The minimally invasive valve surgery in accordance with the present invention simplifies the valve surgery for surgeons and provides beneficial results for patients. The operative procedure allows for a relatively small, e.g., ten centimeter, parasternal incision that makes opening and closing of the chest easier and faster without compromising the surgical exposure or access to the aortic root. Performing aortic repairs or replacements through a right parasternal incision simplifies the surgical technique without increasing the difficulty of the procedure or the technical ability required to perform aortic valve surgery. Further, the smaller incision employed in the procedure results in less bleeding, and a lesser area to become infected.

Moreover, not only does the smaller incision tends to cause less incisional pain in patients, the absence of retraction and the strain placed on the ribs tends to also account for lower incisional pain. Without incisional pain, patients require less postoperative analgesia and are more easily ambulated allowing for earlier discharge from the hospital. Decreased patient morbidity as a result of decreased postoperative discomfort tends to result in shorter length of hospital stays.

The foregoing is a description of preferred exemplary embodiments and best mode of the invention contemplated by applicant at time of filing the application. The invention is not limited to the specific embodiments shown. Rather, the scope of the invention is expressed in the appended claims.

What is claimed is:

1. A method for minimizing invasion in a surgical procedure involving a portion of at least one of the heart and great vessels, comprising the steps of:

making a parasternal incision exposing a predetermined number of costal cartilages;

excising at least one costal cartilage to provide access to the portion of the heart or great vessels of interest, and effecting a surgical procedure through the parasternal incision.

2. The method of claim 1 wherein the step of effecting a surgical procedure comprises the steps of:

occluding the aorta to facilitate establishing a coronary by-pass; and arresting the heart.

3. The method of claim 1 wherein the step of making a parasternal incision comprises making a right parasternal incision extending from the vicinity of the lower edge of the second costal cartilage to the superior edge of the fifth costal cartilage.

4. The method of claim 1 wherein the step of excising at least one costal cartilage comprises the step of excising the third and fourth costal cartilages.

5. The method of claim 1 wherein the step of effecting the surgical procedure comprises performing a surgical procedure involving a portion of at least one of the heart and great vessels, located between a point approximately 3 centimeters above supra annular ridge and the mid ventricular cavity.

6. The method of claim 2 wherein the step of effecting the surgical procedure further comprises performing a surgical procedure involving the aortic valve.

7. The method of claim 1 wherein the step of effecting the surgical procedure comprises replacing the aortic valve.

8. The method of claim 2 wherein the step of effecting the surgical procedure comprises replacing the aortic valve.

9. The method of claim 1 wherein:

the step of making a parasternal incision comprises the step of making a right parasternal incision extending from the vicinity of the lower edge of the second costal cartilage to the superior edge of the fifth costal cartilage;

the step of excising at least one costal cartilage comprises the step of excising the third and fourth costal cartilages, and the step of effecting the surgical procedure comprises the steps of:

establishing a cardiopulmonary by-pass, whereby the heart is excluded from circulation;

incising the aorta to expose the coronary ostia and the aortic valve;

arresting cardiac function;

operating on the aortic valve.

10. The method of claim 9 wherein the step of effecting the surgical procedure further comprises the steps of placing sutures in the vicinity of each commissure of the aortic valve, and placing tension on such sutures.

11. The method of claim 9 wherein the step of effecting the surgical procedure comprises excising the valve cusps of the aortic valve, and securing a replacement valve to the aortic annulus.

12. The method of claim 9 wherein the step of arresting cardiac function comprises infusing cardioplegia directly into the coronary ostia exposed by incising the aorta.

* * * * *